United States Patent
Gross et al.

(10) Patent No.: US 10,908,238 B2
(45) Date of Patent: Feb. 2, 2021

(54) MAGNETIC RESONANCE COIL UNIT AND METHOD FOR ITS MANUFACTURE

(71) Applicants: Brainlab AG, Munich (DE); Siemens Aktiengesellschaft, Munich (DE); pro med instruments GmbH, Freiburg (DE)

(72) Inventors: Patrick Gross, Buckenhof (DE); Tilman Niederführ, Freiburg (DE); Brian Vasey, Munich (DE); Nadja Heindl, Munich (DE); Dimitrios Sapnaras, Munich (DE)

(73) Assignees: BRAINLAB AG, Munich (DE); SIEMENS AKTIENGESELLSCHAFT, Munich (DE); PRO MED INSTRUMENTS GMBH, Freiburg (DE)

( * ) Notice: Subject to any disclaimer, the term of this patent is extended or adjusted under 35 U.S.C. 154(b) by 465 days.

(21) Appl. No.: 15/031,392

(22) PCT Filed: Oct. 25, 2013

(86) PCT No.: PCT/EP2013/072430
§ 371 (c)(1),
(2) Date: Apr. 22, 2016

(87) PCT Pub. No.: WO2015/058815
PCT Pub. Date: Apr. 30, 2015

(65) Prior Publication Data
US 2016/0259019 A1  Sep. 8, 2016

(51) Int. Cl.
*G01R 33/3415* (2006.01)
*G01R 33/48* (2006.01)
(Continued)

(52) U.S. Cl.
CPC .......... *G01R 33/3415* (2013.01); *A61B 5/055* (2013.01); *A61B 5/0555* (2013.01);
(Continued)

(58) Field of Classification Search
CPC .... A61B 2090/3954; A61B 2090/3967; G01R 33/341–33/3415
See application file for complete search history.

(56) References Cited

U.S. PATENT DOCUMENTS 5,394,457 A * 2/1995 Leibinger ................ A61B 6/12
378/162
5,427,099 A * 6/1995 Adams .................... A61K 49/18
378/163
(Continued)

FOREIGN PATENT DOCUMENTS

CN 102859385 A 1/2013
WO 9521582 A1 8/1995

OTHER PUBLICATIONS

Kartmann et al., "Integrated PET/MR imaging: Automatic attenuation correction of flexible RF coils" Medical Physics vol. 40, Issue 8, Aug. 2013 pp. 0182301-1-082301-14.*
(Continued)

*Primary Examiner* — Katherine L Fernandez
*Assistant Examiner* — Colin T. Sakamoto
(74) *Attorney, Agent, or Firm* — Tucker Ellis LLP

(57) ABSTRACT

A magnetic resonance (MR) coil unit, comprising: —an MR coil body which houses at least one MR coil, the MR coil body having a front surface for facing a patient, a reverse surface opposite to the front surface, and at least one opening through the MR coil body which connects the front and reverse surfaces; —at least one MR marker located at
(Continued)

Figure 1:
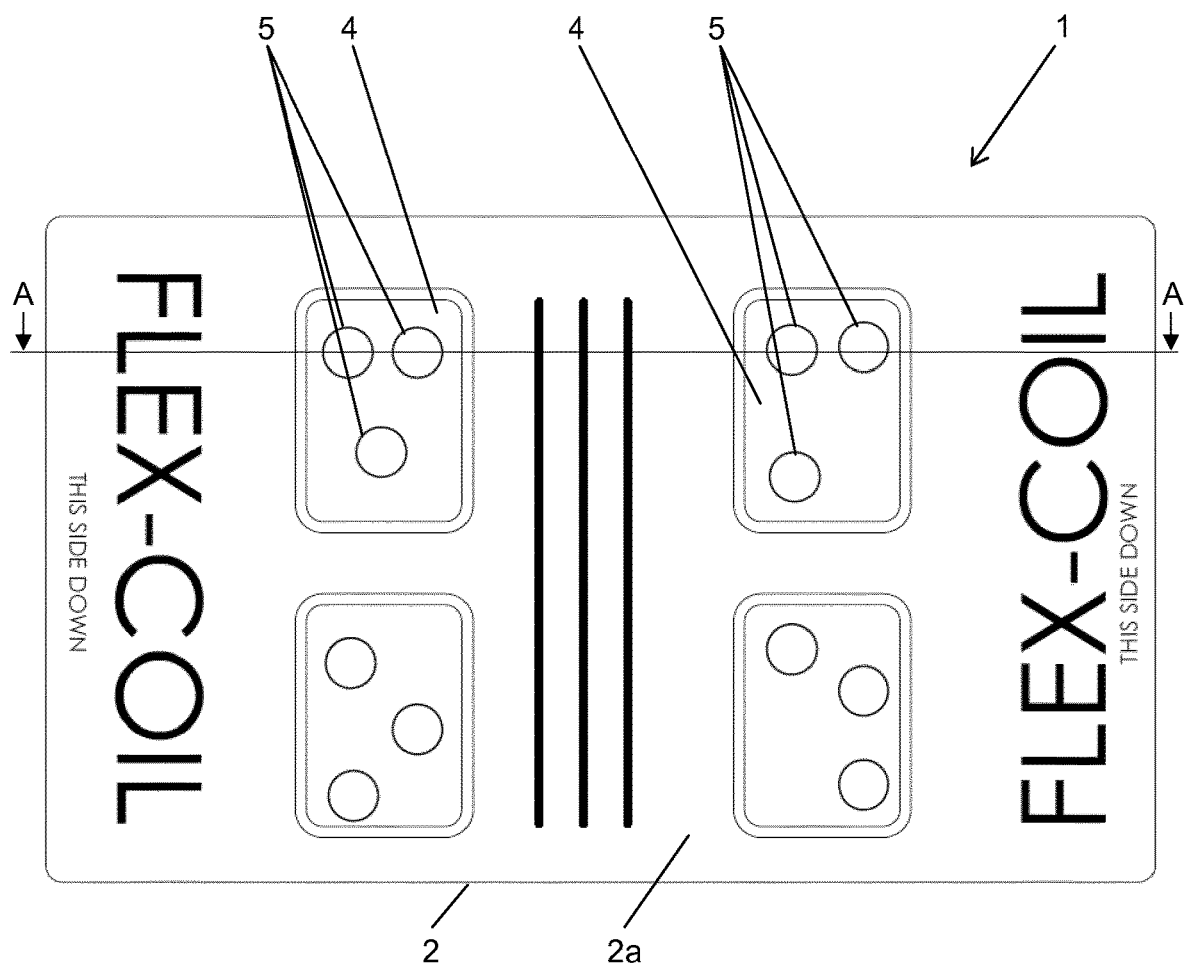

least partly in said at least one opening in the MR coil body; and—at least one optical marker located above the reverse surface of the MR coil body.

20 Claims, 4 Drawing Sheets

(51) Int. Cl.
*A61B 5/055* (2006.01)
*G01R 33/58* (2006.01)
A61B 90/00 (2016.01)
A61B 34/20 (2016.01)
A61B 90/20 (2016.01)

(52) U.S. Cl.
CPC ......... *G01R 33/4808* (2013.01); *G01R 33/58* (2013.01); *A61B 90/20* (2016.02); *A61B 2034/2055* (2016.02); *A61B 2034/2057* (2016.02); *A61B 2090/3937* (2016.02); *A61B 2090/3954* (2016.02); *A61B 2562/12* (2013.01)

(56) References Cited

U.S. PATENT DOCUMENTS

| | | | |
|---|---|---|---|
| 5,466,086 A * | 11/1995 | Goto | E04B 1/2604 403/267 |
| 6,333,971 B2 * | 12/2001 | McCrory | A61K 49/0409 378/162 |
| 8,704,519 B2 * | 4/2014 | Biber | A61B 5/064 324/318 |
| 8,818,490 B2 | 8/2014 | Martens | |
| 9,939,130 B2 * | 4/2018 | Jeung | A61B 5/1127 |
| 2007/0225599 A1 * | 9/2007 | Solar | A61B 90/39 600/426 |
| 2009/0048508 A1 | 2/2009 | Gill | |
| 2009/0112082 A1 | 4/2009 | Piferi et al. | |
| 2010/0156421 A1 * | 6/2010 | Sukkau | G01R 33/3415 324/318 |
| 2010/0296723 A1 * | 11/2010 | Greer | A61B 5/064 382/153 |
| 2013/0035585 A1 | 2/2013 | Martens et al. | |

OTHER PUBLICATIONS

International Search Report, PCT/EP2013/072430, pp. 1-4, European Patent Office (EPO), NL, dated Aug. 5, 2014.

Bangsen et al: "Magnetic Resonance Diagnostics"; People's Health Press; with English translation. Jan. 31, 1995, 11 pages.

Daniel H. Paulus et al. "Simultaneous PET/MR imaging: MR-based attenuation correction of local radiofrequency surface coils", "Nuclear medicine physics" vol. 39, Issue 7. 1 Page.

* cited by examiner

MAGNETIC RESONANCE COIL UNIT AND METHOD FOR ITS MANUFACTURE

RELATED APPLICATION DATA

This application is a national phase application of International Application No. PCT/EP2013/072430 filed Oct. 25, 2013 and published in the English language.

The present invention relates to a magnetic resonance (MR) coil unit, a magnetic resonance unit comprising an MR coil unit and a method for manufacturing an MR coil unit.

Magnetic resonance (MR) is a popular medical imaging modality for obtaining three-dimensional images of a patient. It is also known as magnetic resonance imaging (MRI) or magnetic resonance tomography (MRT). It uses a coil to apply a varying magnetic field in order to cause nuclei in the patient to produce a rotating magnetic field. This magnetic field can be detected, for example using the coil which generates the varying magnetic field or using a separate detection coil.

In many medical workflows, it is advantageous or even required to co-register the MR image with another image of a different modality, such as for example an image of an optical microscope such as is used in neurosurgery. This is accomplished by using MR-visible markers which are visible in the MR image and optical markers which are attached to an MR coil and can be detected by a medical navigation system. The MR markers and the optical markers are in a known spatial relationship, which means that they are fixed in a mutually and geometrically defined, stable and robust configuration. By detecting the position of the MR markers in the MR image and the position of the optical markers and by utilising the known spatial relationship, it is possible to determine the position (meaning the spatial location and/or rotational alignment) of the MR image, for example in a reference co-ordinate system of the medical navigation system. If the position of another imaging apparatus is also determined in the reference co-ordinate system of the medical navigation device, the image obtained using the other imaging apparatus can be co-registered with the MR image. Co-registering images means establishing a positional relationship between the images, such that their positions are known in a common reference (co-ordinate) system.

It is therefore an object of the present invention to provide a magnetic resonance coil unit which is compact in design and which has MR and optical markers which can easily be detected. This is achieved by a magnetic resonance coil unit and a method for manufacturing a magnetic resonance coil unit as claimed in the independent claims.

In accordance with the present invention, a magnetic resonance coil unit comprises an MR coil body which houses at least one MR coil. The MR coil body has a front surface for facing a patient, a reverse surface opposite to the front surface, and at least one opening through the MR coil body which connects the front and reverse surfaces. In a typical configuration, the MR coil body houses an array of loop coils, wherein the loop coils are arranged in a plane which is (basically) parallel to the front surface or the reverse surface of the MR coil body. The opening(s) in the MR coil body then extends/extend through the respective loops, in particular orthogonally with respect to the plane of the coil loops.

The MR coil unit also comprises at least one MR marker located at least partly in said at least one opening in the MR coil body, and at least one optical marker located above the reverse surface of the MR coil body, i.e. within a space delineated by the reverse surface of the MR coil body and outside the MR coil body. This means that the reverse surface is a boundary of said space, but the space can extend over the reverse surface in a direction tangential to the reverse surface. In other words, an optical marker is considered to be located above the reverse surface even if it is located outside the space bounded by the surface normals of the reverse surface situated at the edge(s) of the reverse surface and pointing away from the front surface. In this case, the distance from the optical marker to the reverse surface is smaller than the distance to the front surface.

Using this configuration, the optical marker(s) can easily be detected because it/they face(s) away from the patient. The MR coil unit can thus be placed closer to the patient, which results in a better quality of the MR image. The inventors have found that the MR markers can be sufficiently clearly detected in the MR image even if they are located at least partly in the opening(s) of the MR coil body.

In a preferred embodiment, the at least one MR marker does not protrude beyond the front surface of the MR coil body. This means that the surface of the MR coil unit closest to the patient is the front surface of the MR coil body. The MR coil unit can thus be placed very close to or even in contact with the patient. This is particularly advantageous in terms of increasing the quality of the MR image and/or if the front surface of the MR coil body is padded, thus resulting in increased patient convenience and comfort.

In one particular embodiment, the at least one MR marker is located completely within said at least one opening. This means that the MR marker does not protrude beyond the reverse surface of the MR coil body.

The MR and optical markers are arranged in a known spatial relationship in order to enable the MR image position to be calculated from the position of the optical markers.

The MR coil unit preferably comprises a plurality of MR markers in a known spatial relationship. If there is a plurality of openings through the MR coil body, the MR markers are preferably distributed amongst the plurality of openings. There are preferably at least three MR markers in each of the openings.

In another embodiment, the MR coil unit comprises a plurality of optical markers in a known spatial relationship. In particular, the MR coil unit comprises at least three optical markers, such that the position of the MR coil unit, and in particular the positions of the MR markers, can be calculated from the determined position of the optical markers.

The optical and MR markers are preferably fixed to a common holding bracket. The combination of the holding bracket, the optical markers and the MR markers is also referred to as a marker matrix, and the holding bracket is referred to as the matrix body. Since all the markers are fixed to the same holding bracket or matrix body, a defined, stable and robust spatial relationship between all the markers is guaranteed.

In one embodiment, an MR marker comprises a fill opening which points towards the reverse surface. A liquid having known MR properties can be inserted into or removed from the MR marker through the fill opening. Since the fill opening points towards the reverse surface, and therefore away from the front surface which faces the patient, the liquid can be prevented from leaking onto the patient. The specification that the fill opening points towards the reverse surface of the MR coil body includes the scenario in which the fill opening protrudes beyond the reverse surface, i.e. this specification relates only to the orientation of the MR marker relative to the MR coil body.

In another embodiment, the thickness of the MR coil body in a direction extending between the front and reverse surfaces of the MR coil body is basically identical to the thickness of the MR markers in this direction, i.e. the front-reverse direction of the MR coil body. This has two implications. The first implication is that the size of the MR marker can be maximised in accordance with the thickness of the MR coil body. The second implication is that the thickness of the MR coil body can be adapted to the size of the MR markers if a particular minimum marker size is required.

The present invention also relates to a magnetic resonance unit, comprising: an MR coil unit as described above; a patient support for accommodating the patient; and an MR holder which holds the MR coil unit such that the front surface of the MR coil body faces the patient support. In one version, the MR holder is free-standing next to the patient support, and in another version, the MR holder is connected directly to the patient support by means of a detachable connection. The patient support can for example be a head support such as a skull clamp, a chair or an operating theatre table. In this magnetic resonance unit, the optical markers are guaranteed to face away from the patient.

In one embodiment, the MR unit comprises a medical navigation system including a camera for detecting the optical markers. The camera is aligned such that the optical markers are within the camera's field of view.

The present invention also relates to a method for manufacturing a magnetic resonance (MR) coil unit. The method includes the step of providing an MR coil body which houses at least one MR coil and has a front surface for facing a patient, a reverse surface opposite to the front surface, and at least one opening through the MR coil body which connects the front and reverse surfaces. The MR coil body can be any coil body as described above. The method also includes the step of placing at least one MR marker at least partly in said at least one opening in the MR coil body and placing at least one optical marker above the reverse surface of the MR coil body. A plurality of MR markers are preferably placed in the at least one opening and/or a plurality of optical markers, in particular three (or more) optical markers, are placed above the reverse surface of the MR coil body.

The at least one MR marker is preferably placed in the at least one opening such that it does not protrude beyond the front surface of the MR coil body. The closest part of the MR coil unit to the patient is therefore the front surface of the MR coil body.

The optical and MR markers are preferably fixed to a common holding bracket or matrix body, and the holding bracket is attached to the MR coil body such that the MR marker(s) is/are located at least partly in said at least one opening in the MR coil body and the optical marker(s) is/are located above the reverse surface of the MR coil body. In this embodiment, all the markers, i.e. the MR markers and the optical markers, are in a known spatial relationship and can be simultaneously placed relative to the MR coil body. Attaching the holding bracket to the MR coil body means fixing the bracket to the MR coil body or fixing the MR coil body to the holding bracket.

The present invention also relates to using the magnetic resonance coil unit in performing magnetic resonance imaging.

If data sets, in particular image data sets, are co-registered, then a positional relationship between the data sets is established. In particular, the positions of the areas represented by the data sets are established with regard to a common reference, such as for example a common reference co-ordinate system. The common reference can be the reference of one of the data sets.

It is the function of a marker to be detected by a marker detection device (for example, a camera or an ultrasound receiver or analytical devices such as CT or MRI) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A magnetic resonance (MR) marker is a marker which can be detected in a magnetic resonance image. An MR marker has known properties when it is imaged using MR imaging. An MR marker can be a body filled with an MR fluid, which is a fluid which has known properties in an MR image.

A navigation system, in particular a surgical navigation system, is understood to mean a system which can comprise: a transmitter which emits electromagnetic waves and/or radiation and/or ultrasound waves; a receiver which receives electromagnetic waves and/or radiation and/or ultrasound waves reflected by a marker; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The electronic data processing device in particular determines the spatial location of a marker or the position of an array of markers which are arranged in a known spatial relationship. The navigation data can be stored in the permanent data memory and for example compared with data stored in said memory beforehand.

In the field of medicine, imaging methods are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. Analytical devices in particular are used to generate the image data in apparatus-based imaging methods. The imaging methods are in particular used for medical diagnostics, to analyse the anatomical body in order to generate images which are described by the image data. The imaging methods are also in particular used to detect pathological changes in the human body. However, some of the changes in the anatomical structure, in particular the pathological changes in the structures (tissue), may not be detectable and in particular may not be visible in the images generated by the imaging methods. A tumour represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernible in the image generated by the imaging method. In addition to these tumours, referred to as "enhancing" tumours, it is thought that approximately 10% of brain tumours are not discernible on a scan and are in particular not visible to a user looking at the images generated by the imaging method.

It is within the scope of the present invention to combine one or more features of two or more embodiments to form a new embodiment wherever technically feasible. The scope of the invention also includes manufacturing method steps corresponding to the hardware configuration of the magnetic resonance coil unit.

Figure 2:
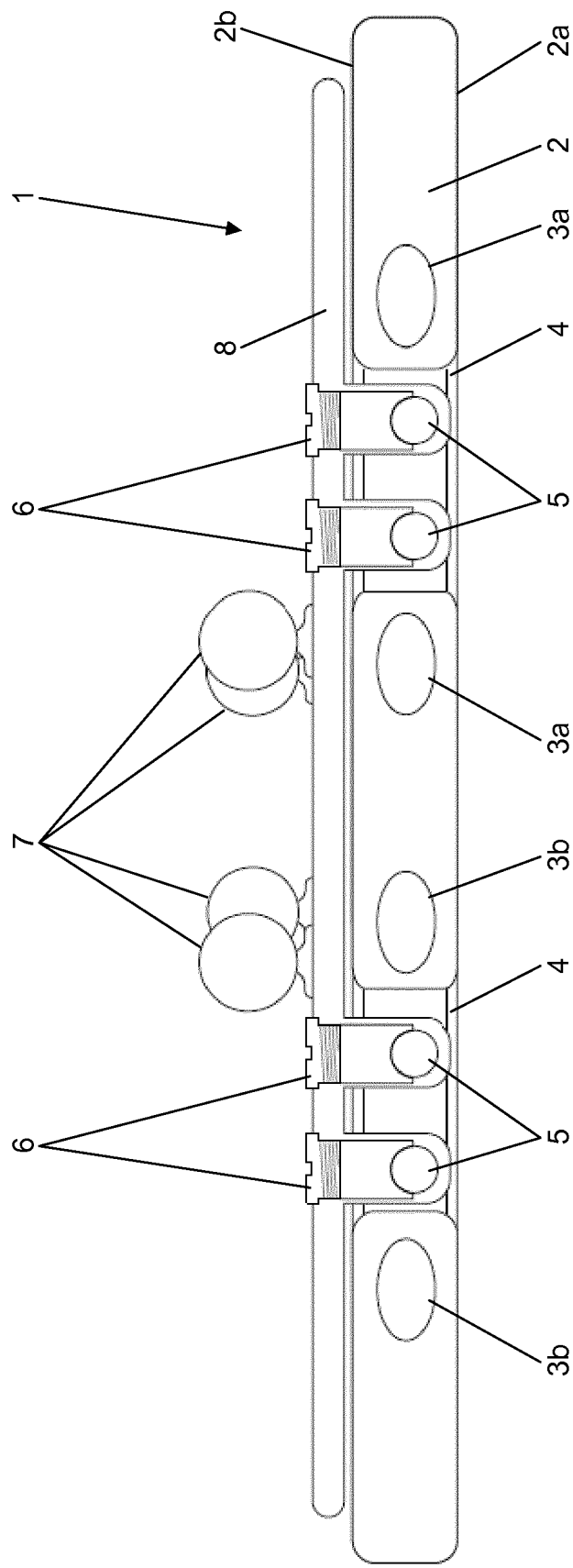
Figure 3:
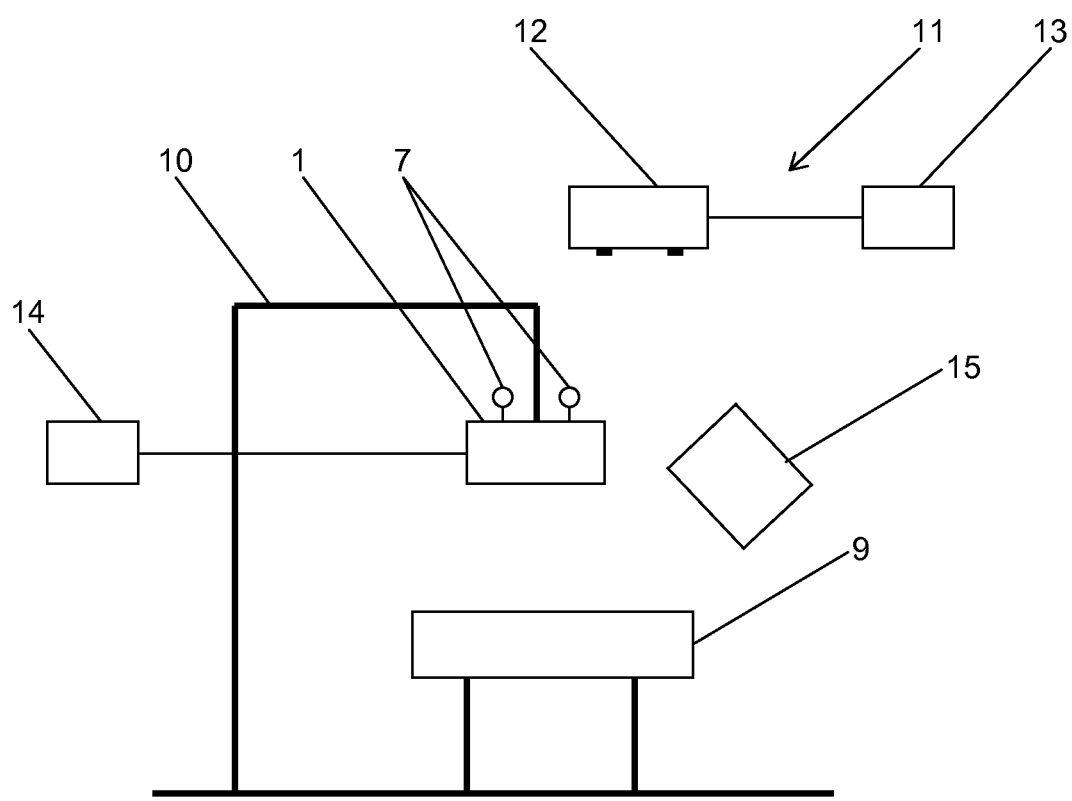

The invention shall now be explained in more detail with reference to the accompanying drawings, which show:

FIG. 1 a plan view of a magnetic resonance coil unit;
FIG. 2 a sectional view of the MR coil unit of FIG. 1;
FIG. 3 a magnetic resonance unit; and
FIG. 4 a magnetic resonance unit with an MR holder connected directly to the patient support.

FIG. 1 shows a plan view of a magnetic resonance coil unit 1 which comprises a magnetic resonance coil body 2 having a front surface 2a which faces a patient when the coil unit 1 is in use. The MR coil unit 1 shown by way of example in FIG. 1 comprises four openings 4 in which MR markers 5 are arranged.

FIG. 2 shows a sectional view of the MR coil unit 1 along the line A-A in FIG. 1. As can be seen in FIG. 2, the MR coil body 2 also has a reverse surface 2b opposite to the front surface 2a. The openings 4 in the coil body 2 extend from the front surface 2a to the reverse surface 2b, thus forming through-holes through the coil body 2. The coil body 2 is made of a flexible material.

MR coils are arranged in the coil body 2. They are loop coils and for example circular in shape. The coils are arranged parallel to the front surface 2a of the coil body 2. Two of the MR coils 3a and 3b are shown in FIG. 2. Each of the MR coils 3a, 3b surrounds an opening 4, such that the openings 4 extend through the interior space enclosed by the MR coils 3a, 3b.

A holding bracket 8, which is also referred to as a matrix body, is attached to the coil body 2. The MR markers 5, which are specific markers for being detected in a magnetic resonance image obtained using the MR coil unit 1, are rigidly attached to the matrix body 8 in a known spatial relationship and such that they protrude into the openings 4 in the coil body 2, but not beyond its front surface 2a. The matrix body 8 is attached to the reverse surface 2b of the coil body 2. Each of the MR markers 5 has a fill opening for adding a suitable fluid to or removing said fluid from the respective MR marker 5. Each fill opening is closed by a fill cap 6 which faces towards the reverse surface 2b of the coil body 2, as viewed from the MR marker 5. This means that the openings are aligned away from the front surface 2a but can protrude beyond the reverse surface 2b. The fluid with which the MR markers 5 are filled has particular magnetic properties which make the MR marker 5 easy to detect in the MR image.

Optical markers 7, which are specific markers for being detected by a camera of a medical navigation system, are also rigidly attached to the matrix body 8 in a known spatial relationship. In the embodiment shown, each optical marker 7 is a marker sphere with a surface coating which is suitable for reflecting infrared light. The spatial relationship between the positions of the MR markers 5 and the optical markers 7, i.e. all the markers which are rigidly attached to the matrix body 8, is known.

In the embodiment shown, the MR markers 5 are formed by a volume which is filled with the MR fluid. The walls of the volume are integrally formed with the matrix body 8, for example in a common moulding step. The volume is closed by the fill cap 6. The optical markers 7 are preferably connected to the matrix body 8 via a threaded post. The optical markers 7 are coated with an IR-reflective coating. Alternatively, the MR markers 5 and/or the optical markers 7 are manufactured independently of the matrix body 8 and are then rigidly attached to the matrix body 8.

The matrix body 8 also has a front surface and a reverse surface. The front surface of the matrix body 8 faces the reverse surface 2b of the coil body 2, such that the reverse surface of the matrix body 8, which is opposite to the front surface of the matrix body 8, faces away from the coil body 2. The optical markers 7 are arranged on the reverse surface of the matrix body 8, which means that they are located above the reverse surface 2b of the MR coil body 2. Since the optical markers 7 are arranged above the reverse surface 2b of the MR coil body 2, they are located closer to the reverse surface 2b of the MR coil body 2 than to the front surface 2a of the MR coil body 2. The optical markers 7 are arranged outside the MR coil body 2.

FIG. 3 shows a magnetic resonance (MR) unit, comprising: the MR coil unit 1; a patient support 9, such as an operating theatre table, for accommodating a patient; and an MR holder 10 which holds the MR coil unit 1 such that the front surface 2a of the MR coil body 2 faces the patient support 9. This means that the optical markers 7 face away from the patient support 9 relative to the coil body 2. As schematically shown in FIG. 3, the MR coil unit 1 is connected to imaging electronics 14 for generating an MR image using the MR coil unit 1. FIG. 3 also shows a medical navigation system 11, comprising a stereoscopic infrared camera 12 and navigation system electronics 13. The stereoscopic camera 12 is arranged such that the optical markers 7 are within its field of view. The stereoscopic camera 12 captures a stereoscopic image showing at least the optical markers 7. The navigation system electronics 13 calculate the position of the optical markers 7 in a reference co-ordinate system of the medical navigation system 11 from the images provided by the stereoscopic camera 12. Since the spatial relationship between the optical markers 7 and the MR markers 5 is known, it is possible to calculate the locations of the MR markers 5 in the co-ordinate system of the medical navigation system 11. If the locations of the MR markers 5 are also determined in the MR image, then it is possible to calculate the alignment of the MR image in the co-ordinate system of the medical navigation system 11.

An optical microscope 15 is also provided as an example of an image generating unit. The optical microscope 15 also carries optical markers (not shown). The locations of the optical markers of the optical microscope 15 can be determined using the medical navigation system 11. The alignment of an image generated using the optical microscope 15 in the co-ordinate system of the medical navigation system 11 can then be calculated from these locations. As a result, the MR image can be co-registered with the image generated by the optical microscope 15.

Figure 4:
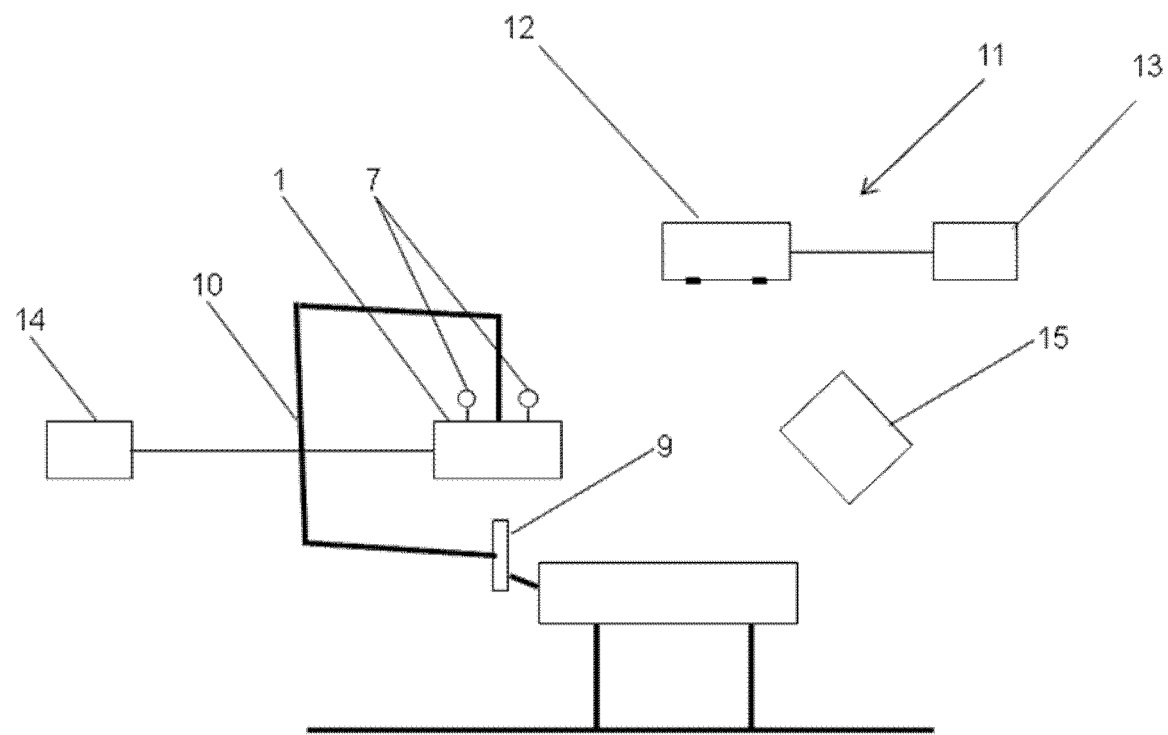

FIG. 4 shows a magnetic resonance (MR) unit as described in FIG. 3, wherein the patient support (9) is a head support or skull clamp supporting a patient's head. The MR holder (10) which holds the MR coil unit 1 as described in FIG. 3 is directly connected to the patient support (9) by means of a detachable connection.

The invention claimed is:

1. A magnetic resonance (MR) coil unit, comprising:
   at least one MR coil;
   an MR coil body that houses the at least one MR coil, the MR coil body having a front surface for facing a patient, a reverse surface opposite to the front surface, and at least one opening extending through the MR coil body in an interior space surrounded by the at least one MR coil and connecting the front and reverse surfaces; and
   a matrix body positioned above the at least one MR coil, comprising:
      a front surface that is attached to the reverse surface of the MR coil body;
      a reverse surface;
      at least one MR marker that is rigidly attached to the front surface of the matrix body such that the at least one MR marker protrudes at least partly into the at least one opening in the MR coil body below the front surface of the matrix body such that the at least one MR marker is surrounded by the at least one MR coil; and
      at least one optical marker that is rigidly attached to the reverse surface of the matrix body such that the at least one optical marker is located above the reverse surface of the MR coil body, wherein the at least one optical marker is rigidly attached at a location of the matrix body such that the at least one optical marker is spaced from the at least one MR marker in a direction parallel to the front surface of the matrix body.

2. The MR coil unit according to claim 1, wherein the at least one MR marker does not protrude over the front surface of the MR coil body.

3. The MR coil unit according to claim 1, wherein the at least one MR marker is completely located in the at least one opening.

4. The MR coil unit according to claim 1, wherein the at least one MR marker comprises a plurality of MR markers in a structurally fixed spatial relationship.

5. The MR coil unit according to claim 1, wherein the at least one optical marker comprises a plurality of optical markers in a predetermined spatial relationship.

6. The MR coil unit according to claim 1, wherein the at least one MR marker comprises a fill opening pointing towards the reverse surface of the MR coil body.

7. The MR coil unit according to claim 1, wherein the at least one MR coil includes at least two MR coils, the at least one opening includes at least two openings extending through the MR coil body enclosed by a respective one of the at least two MR coils, and the at least one MR marker includes two MR markers each located completely in a respective one of the at least two openings.

8. The MR coil unit of claim 1, wherein the at least one optical marker is configured to be detected by a camera of a medical navigation system, the medical navigation system determining a location of the at least one MR marker using a fixed spatial relationship between the at least one MR marker and the at least one optical marker.

9. The MR coil until of claim 1, wherein the at least one MR marker is formed by walls of a volume that is filled with an MR fluid, the walls of the volume being integrally formed with the matrix body.

10. The MR coil until of claim 9, wherein the walls of the volume are integrally formed in a common mould with the matrix body.

11. The MR coil unit of claim 9, wherein the at least one MR marker includes at least two MR markers rigidly attached to the front surface of the matrix body such that the at least two MR markers are completely located in the at least one opening in the MR coil body below the front surface of the matrix body such that the at least two MR markers are surrounded by the at least one MR coil, and wherein the matrix body further comprises at least one fill cap removably secured to the matrix body.

12. A magnetic resonance (MR) unit, comprising:
   an MR coil unit according to claim 1;
   a patient support for accommodating a patient; and
   an MR holder holding the MR coil unit such that the front surface of the MR coil body faces the patient support.

13. The MR unit according to claim 12, further comprising a medical navigation system including a camera for detecting the at least one optical marker, wherein the camera is aligned such that the at least one optical marker is within the camera's field of view.

14. The MR unit according to claim 12, wherein the MR holder is directly connected to the patient support.

15. The MR unit of claim 13, wherein the medical navigation system determining a location of the at least one MR marker using a fixed spatial relationship between the at least one MR marker and the at least one optical marker.

16. A method for manufacturing a magnetic resonance (MR) coil unit, comprising:
   providing an MR coil body housing at least one MR coil, the MR coil body having a front surface for facing a patient, a reverse surface opposite to the front surface, and at least one opening through the MR coil body in an interior space surrounded by the at least one MR coil and connecting the front and reverse surfaces;
   providing a matrix body having a front surface and a reverse surface; rigidly attaching at least one MR marker to the front surface of the matrix body such that the front surface of the matrix body is attached to the reverse surface of the MR coil body, the at least one MR marker at least partly protrudes into the at least one opening in the MR coil body and is surrounded by the at least one MR coil; and
   rigidly attaching at least one optical marker to the reverse surface of the matrix body such that the at least one optical marker is located above the reverse surface of the MR coil body and such that the at least one optical marker is spaced from the at least one MR marker in a direction parallel to the front surface of the matrix body.

17. The method according to claim 16, wherein the at least one MR marker is rigidly attached to the front surface of the matrix body such that no portion of the at least one MR marker protrudes over the front surface of the MR coil body.

18. The method for manufacturing a MR coil unit of claim 16, wherein the at least one optical marker is configured to be detected by a camera of a medical navigation system, the medical navigation system determining a location of the at least one MR marker using a fixed spatial relationship between the at least one MR marker and the at least one optical marker.

19. The method for manufacturing a MR coil unit according to claim 16, wherein the at least one MR marker is formed by a volume having walls, which is filled with an MR fluid, the walls of the volume being integrally formed with the matrix body.

20. The method for manufacturing a MR coil unit according to claim 19, wherein the walls of the volume are integrally formed with the matrix body via common moulding.

* * * * *